United States Patent [19]

Crawford et al.

[11] Patent Number: 4,994,457

[45] Date of Patent: Feb. 19, 1991

[54] ANTIINFLAMMATORY COMPOSITIONS AND METHODS

[75] Inventors: Thomas C. Crawford, Ledyard; David L. Larson, East Lyme; Joseph G. Lombardino, Niantic, all of Conn.

[73] Assignee: Pfizer Inc., New York, N.Y.

[21] Appl. No.: 66,352

[86] PCT No.: US85/01926
§ 371 Date: May 19, 1987
§ 102(e) Date: May 19, 1987

[22] PCT Filed: Oct. 2, 1985

[51] Int. Cl.$^5$ .................... A61K 31/54; A61K 49/00
[52] U.S. Cl. .................... 514/226.5; 424/10; 514/922; 514/925; 514/927
[58] Field of Search ............ 424/10; 514/922, 226.5, 514/925, 927, 400

[56] References Cited

U.S. PATENT DOCUMENTS

| | | | |
|---|---|---|---|
| 4,376,768 | 3/1983 | Ozaki et al. | 424/246 |
| 4,434,163 | 2/1984 | Lombardino | 424/246 |
| 4,434,164 | 2/1984 | Lombardino | 424/246 |
| 4,551,452 | 11/1985 | Marfat | 514/222 |
| 4,559,326 | 12/1985 | Crawford et al. | 514/420 |
| 4,564,614 | 1/1986 | Crawford et al. | 514/222 |

FOREIGN PATENT DOCUMENTS

| | | | |
|---|---|---|---|
| 2426106 | 1/1975 | Fed. Rep. of Germany | 514/162 |
| 2078738 | 1/1982 | United Kingdom | |
| 8400490 | 2/1984 | World Int. Prop. O. | |

OTHER PUBLICATIONS

Dobrescu et al., Chem. Abstr. 79(3):16639g (1973).
The Merck Index, 10th Ed., 1983, p. 658, No. 4452.
Chemical Abstracts 83, 188283K, 1975; abstracting Ishii et al., Nippon Yakurigaku Zasshi, 70(6), 863–9 (1974).
Chemical Abstracts 81, 99415w, 1974; abstracting Fukawa et al., Oyo Yakuri 7(9–10); 1339–48 (1973).
Chemical Abstracts 66, 112545a, 1967; abstracting Bole et al., J. Lab. Clin. Med. 69(4), 610–23 (1967).
Urushidani et al., Japan J. Pharmacol., vol. 27, pp. 316–319 (1977).
Tanaka et al., Japan J. Pharmacol., vol. 32, pp. 307–313 (1982).
Kunimi et al., Japan J. Pharmacol., vol. 32, pp. 469–477 (1982).
Lim et al., J. Pharm. Sci., vol. 68, pp. 295–298 (1979).

Primary Examiner—Jerome D. Goldberg
Assistant Examiner—Theodore J. Craires
Attorney, Agent, or Firm—Peter C. Richardson; J. Trevor Lumb; Robert K. Blackwood

[57] ABSTRACT

An improved antiinflammatory composition and method of treating inflammation which employs a combination of a non-steroidal antiinflammatory agent such as piroxicam, or a pharmaceutically acceptable salt thereof, with 5'-guanylic acid or N-acetyl-L-methionine, or a pharmaceutically acceptable salt thereof.

26 Claims, No Drawings

ANTIINFLAMMATORY COMPOSITIONS AND METHODS

BACKGROUND OF THE INVENTION

The present invention is concerned with an improved antiinflammatory composition and method of treating inflammation which employs a non-steroidal antiinflammatory agent such as piroxicam, or a pharmaceutically acceptable salt thereof (particularly the ethanolamine salt of piroxicam), in combination with N-acetyl-L-methionine or 5'-guanylic acid, or a pharmaceutically acceptable salt thereof. The generic names used here and elsewhere herein are from the USAN and the USP Dictionary of Drug Names, 1961-1981, Griffiths et al., ed., U.S. Pharmacopeial Convention Inc., Rockville, Md., 1984, and/or appear as the primary names in The Merck Index 10th Edition. The alternative systematic name for piroxicam, having the formula

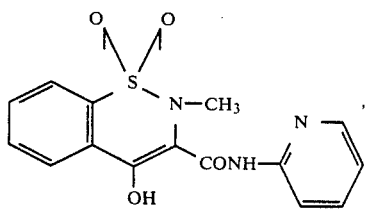

is 4-hydroxy-2-methyl-N-2-pyridinyl-2H-1,2-benzothiazine-3-carboxamide 1,1-dioxide (The Merck Index 10th Ed., Monograph No. 7378 and page REG-68). Alternative names for 5'-guanylic acid, having the formula

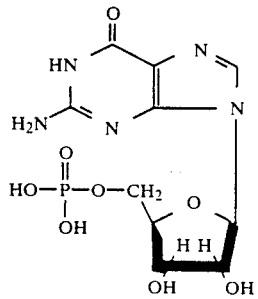

are guanosine 5'-monophosphate and guanine riboside-5-phosphoric acid (Merck Index, 10th Ed.).

Gastrointestinal irritation, including ulcers, is a side effect commonly associated, to one degree or another, with antiinflammatory agents. In many cases, individuals requiring such antiinflammatory treatment are precluded from enjoying the benefits thereof because of their susceptibility to such side effects. The present combination of a non-steroidal antiinflammatory agent with 5'-guanylic acid or N-acetyl-L-methionine permits desirable antiinflammatory therapy while preventing or ameliorating said gastrointestinal irritation or ulcers.

As noted in The Merck Index, 10th Edition, the DL form of N-acetylmethionine finds therapeutic use as a lipotropic, while 5'-guanylic acid, in the form of its disodium salt, is used as a flavor intensifier. There are no known reports bearing on the use of these compounds to reduce gastric side effects of non-steroidal antiinflammatory agents or to reduce the effects of ulcers under any circumstances. The aluminum salts of either N-acetyl-L-glutamine or N-acetyl-L-carnosine [N-(N-acetyl-beta-alanyl)-L-histidine], but not N-acetyl-L-carnosine or L-carnosine per se, have been reported to prevent the exacerbation of gastric ulcers in rats by certain antiinflammatory agents [Tanaka et al., Japan. J. Pharmacol., v. 32, pp. 307-313 (1982); Kunimi et al., loc. cit., pp. 469-477 (1982)]. On the other hand, certain amino acids, including methionine, have been reported to inhibit gastrointestinal ulcers induced by the subcutaneous injection of indomethacin [Urishidani et al., Japan. J. Pharmacol. 27, pp. 316-319 (1977)] and to have a beneficial effect on the gastric mucosal damage of aspirin solutions in rats [Lim et al., J. Pharm. Sci. 68, pp. 295-298 (1979)].

SUMMARY OF THE INVENTION

The present invention concerns an improved antiinflammatory composition which comprises an antiinflammatory amount of piroxicam or a pharmaceutically acceptable salt thereof in combination with a gastric antiirritation and ulcer inhibiting amount of N-acetyl-L-methionine or 5'-guanylic acid, or a pharmaceutically acceptable salt thereof.

The present invention is also concerned with an improved method for the treatment of inflammation in mammal, including man, which comprises, in addition to treatment with an antiinflammatory amount of said piroxicam or salt, treatment with a gastric antiirritation and ulcer inhibiting amount of said guanylic acid, or salt.

As used herein the term "pharmaceutically-acceptable salts" is generally intended to refer to cationic salts such as the alkali metal salts, e.g., sodium and potassium; alkaline earth metal salts, e.g., calcium and magnesium; ammonium salts; and salts with organic bases, e.g., amines such as ethanolamine, benzathine (N,N'-dibenzylethylenediamine), choline, diethanolamine, ethylenediamine, meglumine (N-methylglucamine), benethamine (N-benzylphenethylamine), diethylamine, piperazine and tromethamine (2-amino-2-hydroxymethyl-1,3-propanediol). The preferred salts are the ethanolamine salt of piroxicam (U.S. Pat. No. 4,434,164), and the near neutral disodium and dipotassium salts of 5'-guanylic acid and the sodium and potassium salts of N-acetyl-L-methionine. Those salts which are not specifically available in the prior art are readily prepared by standard methods of neutralization, concentration, extraction, precipitation and crystallization which are well known in the chemical arts.

DETAILED DESCRIPTION OF THE INVENTION

The clinical value of the present improved formulations in inhibiting gastric irritation and ulcers induced by piroxicam is reflected by appropriate animal studies. Typical experimental protocols, in which the ability of the test compound to prevent or reduce such induced gastric lesioning was determined, are found in the specific Examples below.

The present invention is readily carried out. Piroxicam (or an equivalent amount of its salt) is dosed in a mammal, particularly man, in its usual range, e.g., 0.1 to 1 mg/kg/day, generally as a single daily dose. The guanylic acid (or an equivalent amount of its salt), which if desired can be dosed separately in single or multiple daily dosage, is generally dosed in the range of 0.4-40 mg/kg/day. Likewise the acetylmethionine (or an equivalent amount of its salt), except that higher dosages (in the range of 3-70 mg/kg/day) are generally employed.

Preferably and conveniently, the piroxicam agent and the guanylic acid or acetylmethionine are co-administered in a single, combined formulation. This can be in a form suitable for parenteral administration, but is preferably in a form suitable for oral administration. The proportion of each drug in the combined dosage form will be in the ratio of the total daily dosage of each drug when dosed alone, in amounts suitable for single or divided daily doses as desired. Single daily dosage is preferred in view of the long in vivo half-life of piroxicam. The most preferred combinations are the ethanolamine salt of piroxicam with the disodium or dipotassium salt of 5'-guanylic acid or the sodium or potassium salt of N-acetyl-L-methionine.

In the preferred, oral route of administration, the amount of piroxicam (or salt equivalent) for an average adult patient will generally be in the range of 5-50 mg/day in combination with 25 to 3000 mg/day of the guanylic acid or 200 to 5000 mg/day of the acetylmethionine, an amount generally sufficient to inhibit gastrointestinal irritation or ulcers which could otherwise be induced by the piroxicam in patients susceptible to this side effect. Of course, in particular cases, doses outside these ranges will be administered at the discretion of the attending physician.

The combined compounds are administered alone or in further combination with pharmaceutically-acceptable carriers or diluents. For oral use, suitable pharmaceutical carriers include inert diluents or fillers, thereby forming dosage forms such as tablets, powders, capsules, and the like. These pharmaceutical compositions can, if desired, contain additional ingredients such as flavorings, binders, excipients and the like. For example, tablets containing various excipients, such as sodium citrate, are employed, together with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials therefor include lactose or milk sugar and high molecular weight polyethylene glycols.

The present invention is illustrated by the following examples. However, it should be understood that the invention is not limited to the specific details of these examples.

EXAMPLE 1

Protective Effect of Disodium 5'-Guanylate on Piroxicam-Induced Gastric Lesions in Rats Adult male "specific pathogen free" rats weighing 140-160 grams of the CD strain (Sprague-Dawley) were obtained from Charles River Breeding Laboratories (Kingston, N.Y.). The animals were acclimated for approximately one week and tested when they reached a body weight of 200-225 grams. The rats were fasted for 16 hours and randomized into groups consisting of 10 animals which were normalized with regard to their average body weight.

Gastric ulcers were induced in the animals by orally dosing them with a single 120 mg/kg dose of piroxicam (ethanolamine salt) in 2 ml. of aqueous 0.1% methylcellulose (pH=6.8). Those animals receiving disodium 5'-guanylate separately received the second drug in an additional 2 ml. of the same medium at about the same time. Six and one-half hours later, the animals were sacrificed by cervical dislocation and autopsied. The stomachs were surgically removed, dissected along the greater curvature and rinsed with cold water. The stomachs were individually scored for both linear and punctate lesions. The total number of lesions was used for scoring purposes. The data obtained from each group of rats was analyzed after calculation of the mean number $+/-$ the standard error of total gastric lesions. The values obtained were also compared to the controls which received only piroxicam by the two-tailed Student's T-Test for non-paired data. The protective effect of guanylate against piroxicam-induced ulcers is shown in Table I. These data show that disodium 5'-guanylate significantly reduces piroxicam-induced gastric lesions in the healthy fasted rat.

TABLE I

Protective Effect of Disodium 5'-Guanylate Lesions Induced by the Ethanolamine Salt of Piroxicam

| | Oral Dose (mg/kg) | No. of Rats in Group | Lesions/Rat ($\overline{X} +/- SE$)[b] | Significance $p < 0.05$[c] |
|---|---|---|---|---|
| (Control)[a] | 0 | 40 | 8.3 (0.9) | |
| Disodium 5'-Guanylate[a,d] | 1.0 | 20 | 8.1 (0.7) | − |
| | 3.3 | 20 | 5.8 (0.5) | − |
| | 10.0 | 30 | 4.6 (0.8) | + |
| | 33.0 | 40 | 3.9 (0.6) | + |

[a] All animals, including controls, received 120 mg/kg of the ethanolamine salt of piroxicam.
[b] Represents the mean value $\overline{X} +/-$ the standard error (SE).
[c] As determined by the Student's two tailed T-test for non-paired data.
[d] As calculated by linear regression analysis, an $ED_{50}$ (dose of the guanylic acid required to inhibit 50% of control gastric lesions) of 20 mg/kg was determined.

EXAMPLE 2

Protective Effect of N-Acetyl-L-methionine on Piroxicam Induced Gastric Lesions in Rats By the procedure of the preceding Example, the protective effect of the N-acetyl-L-methionine on piroxicam induced gastric lesions in rats was determined. The results are shown in Table II.

TABLE II

Protective Effect of N-Acetyl-L-methionine on Gastric Lesions Induced by the Ethanolamine Salt of Piroxicam

| | Oral Dose (mg/kg) | No. of Rats in Group | Lesions/Rat ($\overline{X} +/- SE$)[b] | Significance $p < 0.05$[c] |
|---|---|---|---|---|
| (Control)[a] | 0 | 50 | 8.0 (0.8) | |
| N-Acetyl-L-methionine[a,d] | 33 | 50 | 6.9 (0.8) | − |
| | 100 | 40 | 3.9 (0.8) | + |
| | 333 | 20 | 3.5 (0.9) | + |

[a] All animals, including controls, received 120 mg/kg of the ethanolamine salt of piroxicam.
[b] Represents the mean value $\overline{X} +/-$ the standard error (SE).
[c] As determined by the Student's two tailed T-test for non-paired data.
[d] The $ED_{50}$ (dose of the N-acetylmethionine required to inhibit 50% of control gastric lesions) is in the range of 100-333 mg/kg.

EXAMPLE 3

Capsules—Piroxicam (20 mg) and N-Acetyl-L-methionine (1000 mg)

The following ingredients are combined in the following proportions by weight:
piroxicam (milled)—20
N-acetyl-L-methionine (milled)—1000 calcium carbonate—250
polyethylene glycol, average—430
molecular weight—4000

The mixture is thoroughly blended so as to obtain a uniform powder. Soft gelatin capsules containing 20 mg. of piroxicam and 1000 mg. of N-acetyl-L-methionine are prepared by filling suitably sized capsules with 1700 mg. of the blend.

To make hard gelatin filled capsules, the amount of inert ingredients is adjusted so as to conveniently fill standard sized gelatin capsules containing the desired amount of each active component.

EXAMPLE 4

Capsules—Piroxicam (10 mg.) and 5'-Guanylic Acid (500 mg.)

The following ingredients are combined in the following proportions by weight:

| | | |
|---|---|---|
| piroxicam ethanolamine salt (milled) | 11.84 | (equivalent to 10 as free acid) |
| dipotassium 5'-guanylate (milled) | 606.25 | (equivalent to 500 as free acid) |
| corn starch | 477.91 | |
| magnesium stearate | 4 | |

The mixture is thoroughly blended so as to form a uniform powder. The resultant mix is filled into appropriately sized hard gelatin capsules (fill weight 1100 mg.) so as to obtain capsules containing the desired potency of each active ingredient.

EXAMPLE 5

Capsules—Piroxicam (20 mg.) and 5'-Guanylic Acid (150 mg.)

The following ingredients are combined in the following proportions by weight:
 piroxicam (milled)—20
 5'-guanylic acid—150
 polyethylene glycol, average—630
 molecular weight—4000

The mixture is thoroughly blended so as to obtain a uniform powder. The resultant mix (800 mg. fill weight) is filled into hard gelatin capsules of a suitable size so as to obtain capsules of the desired potency.

EXAMPLE 6

Tablets—Piroxicam (20 mg.) and 5'-Guanylic Acid (20 mg.)

The following ingredients are combined in the following proportions by weight:

| | | |
|---|---|---|
| piroxicam ethanol amine salt | 23.68 | (equivalent to 20 as free acid) |
| disodium 5'-guanylate monohydrate (milled) | 23.41 | (equivalent to 20 as free acid) |
| lactose | 182 | |
| hydroxypropyl methylcellulose | 3 | |
| sodium starch glycollate | 13.91 | |
| magnesium stearate | 4 | |

The mixture is thoroughly blended to form a uniform powder. Measured volumes of the powder, corresponding to 250 mg. by weight, are compressed into tablets containing the desired potency of each active ingredient.

EXAMPLE 7

Tablets—Piroxicam (10 mg.) and N-acetyl-L-methionine (25 mg.)

The following ingredients are combined in the following proportions by weight:

| | | |
|---|---|---|
| piroxicam ethanolamine salt (milled) | 11.84 | (equivalent to 10 of free acid) |
| sodium salt of N-acetyl-L-methionine | 27.86 | (equivalent to 25 of free acid) |
| lactose | 235.3 | |
| hydroxypropyl methylcellulose | 4 | |
| sodium starch glycollate | 16 | |
| magnesium stearate | 5 | |

The mixture is thoroughly blended to form a uniform powder. The powder, in measured volumes corresponding to 300 mg. by weight, is compressed into tablets containing the desired potency of each active ingredient.

EXAMPLE 8

Tablets—Piroxicam (20 mg.) and 5'-Guanylic Acid (50 mg.)

The following ingredients are combined in the following proportions by weight:

| | | |
|---|---|---|
| piroxicam | 20 | |
| disodium guanylate monohydrate | 58.54 | (equivalent to 50 of free acid) |
| lactose | 241.46 | |
| hydroxypropyl methylcellulose | 4 | |
| sodium starch glycollate | 16 | |
| magnesium stearate | 5 | |

The mixture is blended to a uniform powder and compressed into tablets in measured volumes corresponding to 345 mg. by weight to yield tablets of the desired potency in each drug.

We claim:
1. An improved antiinflammatory composition which comprises:
 (a) an antiinflammatory amount of piroxicam or a pharmaceutically acceptable salt thereof; and
 (b) a gastric antiirritation and ulcer-inhibiting amount of 5'-guanylic acid or a pharmaceutically acceptable salt thereof.
2. A composition of claim 1 wherein the piroxicam is in the form of its ethanolamine salt.
3. A composition of claim 1 wherein the piroxicam is in its free enolic form.
4. A composition of claim 1 wherein the 5'-guanylic acid is in the form of its disodium or dipotassium salt.
5. The composition of claim 2 wherein the 5'-guanylic acid is in the form of its disodium salt.
6. The composition of claim 3 wherein the 5'-guanylic acid is in the form of its disodium salt.
7. An improved method for the treatment of inflammation in a mammal which comprises, in addition to treatment with an antiinflammatory amount of piroxicam, or a pharmaceutically acceptable salt thereof, treatment with a gastric antiirritation and ulcer-inhibiting amount of 5'-guanylic acid or a pharmaceutically acceptable salt thereof.

8. A method of claim 7 wherein the piroxicam is in the form of its ethanolamine salt.

9. A method of claim 7 wherein the piroxicam is in its free enolic form.

10. A method of claim 7 wherein the 5'-guanylic acid is in the form of its disodium or dipotassium salt.

11. The method of claim 8 wherein the 5'-guanylic acid is in the form of its disodium salt.

12. The method of claim 9 wherein the 5'-guanylic acid is in the form of its disodium salt.

13. An improved antiinflammatory composition which comprises:
 (a) an antiinflammatory amount of piroxicam or a pharmaceutically acceptable salt thereof; and
 (b) a gastric antiirritation and ulcer-inhibiting amount of N-acetyl-L-methionine or a pharmaceutically acceptable salt thereof.

14. A composition of claim 13 wherein the piroxicam is in the form of its ethanolamine salt.

15. A composition of claim 13 wherein the N-acetyl-L-methionine is in the form of its sodium or potassium salt.

16. A composition of claim 14 wherein the N-acetyl-L-methionine is in the form of its sodium or potassium salt.

17. The composition of claim 16 wherein the N-acetyl-L-methionine is in the form of its sodium salt.

18. A composition of claim 13 wherein the piroxicam is in its free enolic form.

19. The composition of claim 18 wherein the N-acetyl-L-methionine is in its free acid form.

20. An improved method for the treatment of inflammation in a mammal which comprises, in addition to treatment with an antiinflammatory amount of piroxicam, or a pharmaceutically acceptable salt thereof, treatment with a gastric antiirritation and ulcer-inhibiting amount of N-acetyl-L-methionine or a pharmaceutically acceptable salt thereof.

21. A method of claim 20 wherein the piroxicam is in the form of its ethanolamine salt.

22. A method of claim 20 wherein the N-acetyl-L-methionine is in the form of its sodium or potassium salt.

23. A method of claim 21 wherein the N-acetyl-L-methionine is in the form of its sodium or potassium salt.

24. The method of claim 23 wherein the methionine is in the form of its sodium salt.

25. A method of claim 20 wherein the piroxicam is in its free enolic form.

26. The method of claim 25 wherein the N-acetyl-L-methionine is in its free acid form.

* * * * *